United States Patent [19]

Kumar

[11] Patent Number: 5,618,695
[45] Date of Patent: Apr. 8, 1997

[54] DNA ENCODING HEM-1, A GENE EXPRESSED BY SCLEROSING HEMANGIOMA CELLS

[75] Inventor: Rajiv Kumar, Rochester, Minn.

[73] Assignee: Mayo Foundation for Medical Education and Research, Rochester, Minn.

[21] Appl. No.: 487,810

[22] Filed: Jun. 7, 1995

[51] Int. Cl.$^6$ .......................... C12P 21/06; C07H 21/04; C12N 15/00; C12N 1/20

[52] U.S. Cl. .................. 435/69.1; 435/252.3; 435/320.1; 435/172.3; 435/325; 435/348; 530/350; 536/23.5

[58] Field of Search .................. 435/69.1, 240.1, 435/252.3, 320.1; 530/350; 536/23.5

[56] References Cited

U.S. PATENT DOCUMENTS 5,108,359  4/1992  Granov et al. ....................... 600/9

OTHER PUBLICATIONS

Q. Cai et al., "Inhibition of Renal Phosphate Transport by a Tumor Product in a Patient with Oncogenic Osteomalacia," *N. Eng. J. of Medicine*, 330, 1645 (Jun. 9, 1994).

M.J. Econs et al., "Tumor–Induced Osteomalacia—Unveiling a New Hormone," *N. Eng. J. of Medicine*, 330, 1679 (Jun. 9, 1994).

H. Jouishomme et al., "Further Definition of the Protein Kinase C Activation Domain of the Parathyroid Hormone," *J. of Bone and Mineral Res.*, 9, 943 (Jun. 1994).

G.G. Klee et al., "Multisite Immunochemiluminometric Assay for Simultaneously Measuring Whole–Molecule and Amino–Terminal Fragments of Human Parathyrin," *Clin. Chemistry*, 38, 628 (1992).

R. Kumar et al., "Immunolocalization of Calcitriol Receptor, 24–Hydroxylase Cytochrome P–450, and Calbindin $D_{28k}$ in Human Kidney," *Am. J. of Physiology*, 266, F477 (1994).

E.G. Lufkin et al., "Hyperphosphatemic Tumoral Calcinosis: Effects of Phosphate Depletion on Vitamin D Metabolism, and of Acute Hypocalcemia on Parathyroid Hormone Secretion and Action," *J. of Clin. Endocrinology and Metabolism*, 56, 1319 (1983).

R.A. Meyer, Jr. et al., "Parabiosis Suggests a Humoral Factor is Involved in X–Linked Hypophosphatemia in Mice," *J. of Bone and Mineral Res.*, 4, 493 (Aug. 1989).

T. Nesbitt et al., "Crosstransplantation of Kidneys in Normal and Hyp Mice," *J. of Clin. Investigation*, 89, 1453 (May 1992).

Pawlak et al. (1995) Genomics 26: 151–158.

Lau et al. (1979) Clin. Res. 27(2): A421.

Wilkins et al. (1995) J. Invest. Med. Mtg. Am. Fed. Clin. Res. Western Sect. Feb. 8–11 43(Suppl. 1): 195A.

Wilkins et al. (1995) J. Clin. Endocrin. Metab. 80(5): 1628–1634.

*Primary Examiner*—Robert A. Wax
*Assistant Examiner*—Lisa J. Hobbs
*Attorney, Agent, or Firm*—Schwegman, Lundberg, Woessner & Kluth, P.A.

[57] ABSTRACT

An isolated and purified DNA sequence encoding hemangioma factor-1 is provided. A host cell transformed with a DNA sequence encoding hemangioma factor-1 and a method of introducing and expressing the DNA sequence in a host cell is also provided. A further embodiment of the invention is an expression cassette comprising the isolated and purified DNA sequence encoding hemangioma factor-1.

13 Claims, 5 Drawing Sheets

FIG. 1

DNA ENCODING HEM-1, A GENE EXPRESSED BY SCLEROSING HEMANGIOMA CELLS

STATEMENT OF GOVERNMENT RIGHTS

The present invention was made with the support of the United States Government via grants from the National Institutes of Health (DK 25409 and DK 42971). The government has certain rights in the invention.

BACKGROUND OF THE INVENTION

Phosphorus plays an important role in normal human physiology. It is a constituent of nucleic acids, phospholipids, high energy intermediates, and hydroxyapatite which in turn is the major component of bone mineral. Phosphorus is absorbed by and secreted into the intestine, and inorganic phosphates are filtered by the renal glomerulus and reabsorbed by the proximal tubule of the kidney. Thus, the intestine and kidney play key roles in controlling phosphorus homeostasis.

Several factors alter the efficiency with which the intestine and kidney absorb or reabsorb phosphorus. Important among these are the amount of phosphorus ingested in the diet and the rate of sodium reabsorption in the proximal tubule. Hormones such as 1,25-dihydroxyvitamin $D_3$, parathyroid hormone (PTH), growth hormone, insulin-like growth factor and insulin alter the efficiency of phosphate retention in the organism by acting on intestinal or renal epithelia. The effects of 1,25-dihydroxyvitamin $D_3$, and parathyroid hormone, however, are primarily on calcium absorption whereas the effects of growth hormone, insulin-like growth factor and insulin are primarily on anabolic phenomena, cell growth and glucose metabolism. Clearly, the ability of the organism to control phosphorus balance independent of calcium balance would be of biological and homeostatic advantage. A factor (or factors) that specifically alters phosphorus metabolism independent of changes in other metabolic pathways has not been characterized.

Cai et al. (*New Eng. J. Med.*, 330, 1645 (1994)) described the presence of a heat labile, 8,000–25,000 dalton, inhibitor of renal epithelial cell sodium-dependent phosphate transport in supernatants of cultured sclerosing hemangioma cells. These cells were derived from a tumor of a patient with oncogenic osteomalacia and hypophosphatemia. The patient's hypophosphatemia and urinary phosphate wasting were cured upon removal of the tumor. The factor(s) specifically inhibited renal epithelial phosphate transport but not glucose or alanine transport. Supernatants from these tumor cells also contained a substance that cross-reacted with PTH-like antisera but not PTH-related antisera. The mechanism of action of the factor(s) was distinct from that of PTH because the factor(s) inhibited phosphate transport in renal epithelial cells without increasing cAMP concentrations and its action was not blocked by a PTH antagonist. parathyroid hormone antibodies. However, the factor was not further characterized.

Thus, them is a need to identify and isolate genes that encode factors that alter phosphate uptake in the kidney.

SUMMARY OF THE INVENTION

The present invention provides an isolated and purified DNA molecule comprising a DNA segment encoding hemangioma factor-1 (HEM-1). An isolated and purified DNA molecule comprising a DNA segment consisting of SEQ ID NO:1 is also provided. These DNA molecules are double-stranded or single-stranded, preferably, they are cDNA. For example, the DNA molecule encoding the HEM-1 of SEQ ID NO:2 is depicted under amino acids residues 1–381, and is designated SEQ ID NO:1. Another embodiment of the invention is an isolated protein having an amino acid sequence corresponding to SEQ ID NO:2.

An isolated and purified DNA molecule, such as a probe or a primer, of at least seven nucleotide bases which hybridizes to these DNA molecules under stringent conditions is also provided by the invention. The present invention provides a probe or a primer comprising at least seven nucleotide bases of any of the above-disclosed DNA sequences detectably labeled or having a binding site for a detectable label. Such probes or primers are useful to detect, quantify and amplify complementary DNA strands in eukaryotic tissue samples with sequences related to HEM-1.

As used herein, the terms "isolated and/or purified" refer to in vitro isolation of a DNA molecule, or peptide, from its natural cellular environment, and from association with other coding regions of the cellular genome from which it was derived, so that it can be sequenced, replicated and/or expressed.

The present invention also provides an expression cassette, preferably a linear vector, comprising an isolated and purified DNA molecule comprising a DNA segment encoding HEM-1, operably linked to a promoter functional in a host cell. Preferably, the DNA segment is SEQ ID NO:1. Such expression cassettes can be placed into expression vectors which are then employed to transform prokaryotic or eukaryotic host cells. The present vectors can also contain a DNA sequence which is a selectable marker gene or reporter gene, as described below.

The present invention also provides a transformed host cell, the genome of which has been augmented by a non-native DNA sequence encoding HEM-1. Preferably, the non-native DNA sequence is integrated into the chromosome of the transformed host cell.

The present invention also provides a method of introducing and expressing an exogenous HEM-1 gene into a host cell comprising: transforming host cells in vitro with an expression cassette comprising a DNA molecule encoding a HEM-1 gene operably linked to a promoter functional in the host cell; and identifying a transformed host cell which expresses the DNA molecule. This method also provides isolated recombinant HEM-1 protein(s) which is recovered as a product of the transformed host cells, when the cells are cultured under appropriate conditions.

Another embodiment of the invention is an isolated and purified DNA molecule from a sclerosing hemangioma which, when introduced and expressed in a host cell, functions to alter the phosphate uptake of kidney cells. Preferably, the isolated and purified DNA molecule encodes a protein recognized by anti-parathyroid antibodies.

BRIEF DESCRIPTION OF THE FIGURES

FIG. 1 is the nucleotide sequence of a cDNA clone of HEM-1 (SEQ ID NO:1) and its corresponding predicted amino acid sequence (SEQ ID NO:2). Nucleotide residues are numbered in the 5' to 3' direction.

DETAILED DESCRIPTION OF THE INVENTION

Figure 2:
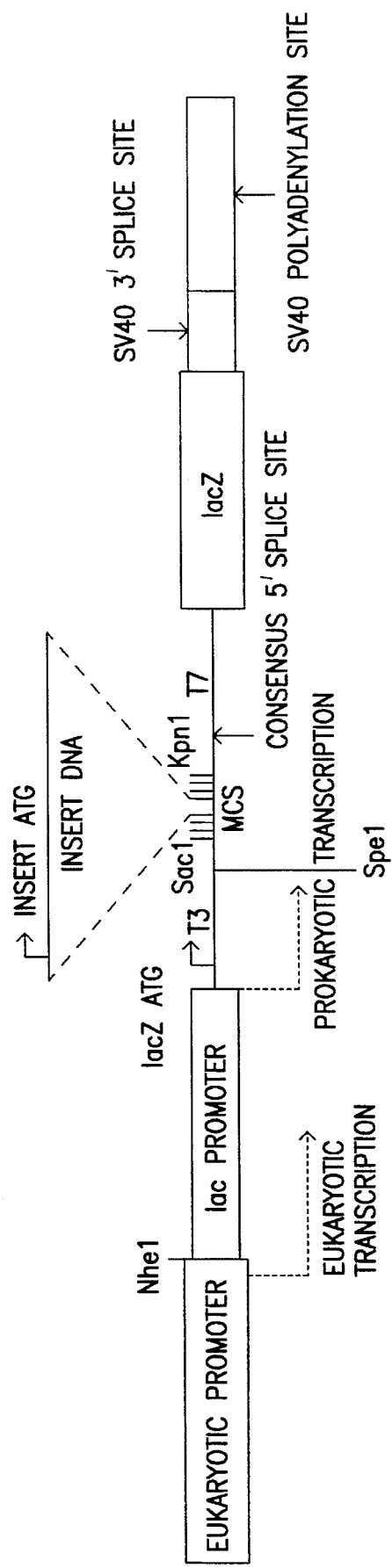
FIG. 2 is a schematic diagram of an expression cassette, pBK.
Figure 3:
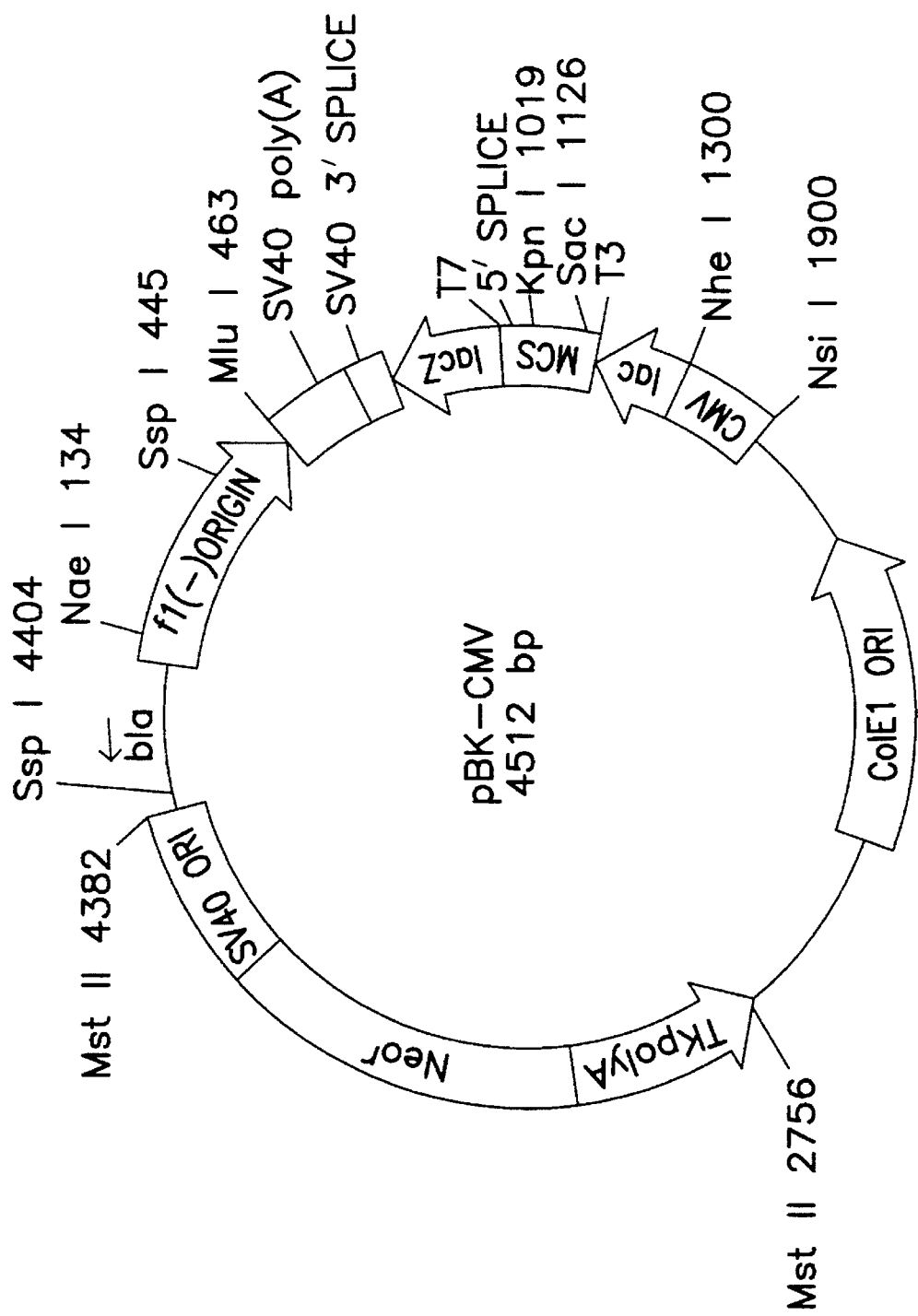
FIG. 3 is a schematic diagram at an expression plasmid, pBK-CMV, useful in expressing a gene of interest in a eukaryotic host cell. pBK-CMV also contains a selectable marker gene.

In order to provide a molecular basis for the factor(s) expressed by sclerosing hemangioma cells that alter phosphate uptake in the kidney, a cDNA expression library derived from a sclerosing hemangioma was screened with anti-PTH antibodies. Previously, Cai et al. (*New Eng. J. Med.*, 330, 1645 (1994)) had shown that a factor(s) recognized by anti-PTH antibodies was present in the supernatant of cultured sclerosing hemangioma cells. Cloning a cDNA for this factor(s) can provide information regarding the molecular mechanism underlying the regulation of kidney phosphate uptake.

Moreover, the identification and isolation of the DNA encoding the factor(s) can provide a clinically useful diagnostic test, as well as molecular-based therapeutics. Once the factor has been identified, an antibody specific for the factor can be made. Patient sera or plasma can then be incubated with the antibody to determined if the factor is present in the patient in an amount different than that found in patients without an alteration in kidney phosphate uptake. Furthermore, the cloning of the gene encoding the factor will elucidate the molecular mechanism giving rise to the presence of this factor in patients with an alteration in phosphate transport in kidney cells, relative to patients without this alteration. Molecular genetic-based therapies directed to controlling the expression of this gene can then be employed.

Other factors expressed by sclerosing hemangioma cells may be useful for defining the molecular basis for the tumorigenicity of these cells, or clarifying the role that the PTH-like immunoreactive protein found in the supernatant of the cultured tumor cells has to the PTH-like immunoreactive moiety found lining the vascular spaces of the tumor tissue (see below). The PTH-like factor found in the supernatant may be secreted by these endothelial cells. The PTH-reactive protein found in the supernatant may be indirectly or directly involved in the regulation of phosphate uptake by kidney cells. Indirect regulation includes, but is not limited to, transcriptional or translational regulation of a factor that directly acts on kidney cells to alter phosphate uptake. The PTH-like reactive protein expressed by the endothelial cells in the tumor may also be involved in aberrant endothelial cell proliferation or function.

Figure 1:
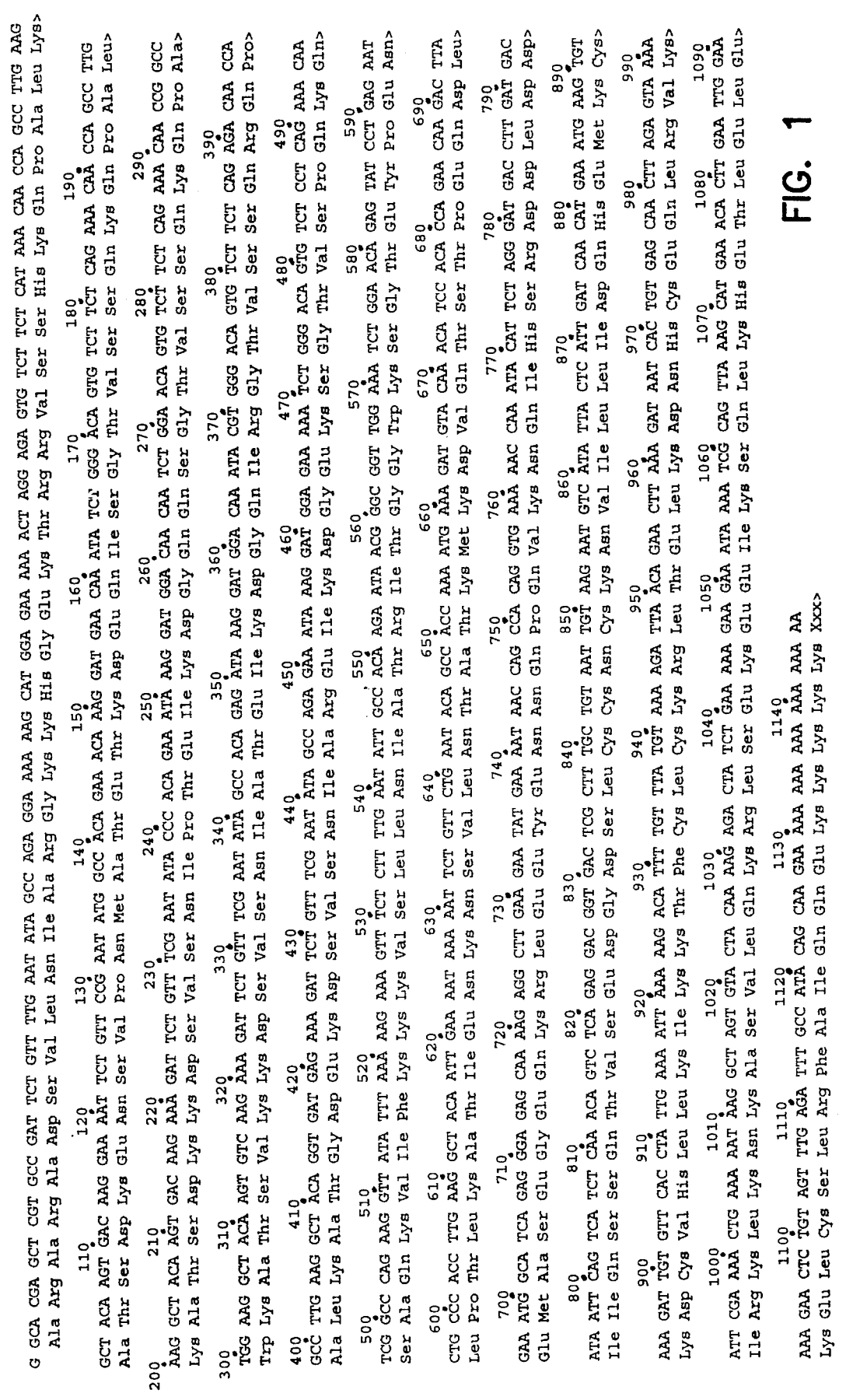

Specifically, the present invention provides an isolated and purified cDNA molecule such as that represented by the complete nucleotide sequence shown in FIG. 1 (SEQ ID NO:1), which comprises a DNA sequence encoding hemangioma factor-1 (HEM-1). The present invention further provides an isolated amino acid sequence consisting of the complete amino acid sequence shown in FIG. 1 (SEQ ID NO:2).

The probes and primers of the present invention are useful for detecting the expression of the DNA molecules of the present invention, and amplifying nucleic acid sequences that fall within the scope of the present invention. The uses of probes and primers, as well as their isolation, purification and conditions under which they are employed for the detection or amplification of a specific gene, are well known in the art.

The present invention also provides isolated and purified DNA molecules which provide "anti-sense" mRNA transcripts of the DNA sequences shown in FIG. 1 which, when expressed from an expression vector in a host cell, can alter phosphate uptake by kidney cells by binding the factor(s) responsible for inhibiting phosphate uptake.

The polymorphic cDNA sequences of the present invention can be introduced into the genome of cell lines, whether mammalian, bacterial, or insect cell lines, by in vitro techniques known in the art, to yield a transfected cell line having the cDNA stably integrated into its genome, so that the DNA molecules of the present invention are expressed by the cell lines. That is, the present invention also provides a transfected cell line having a genome augmented by a recombinant (non-native) DNA sequence, preferably by a chromosomally integrated recombinant (genetically engineered) DNA sequence that includes a gene for encoding for HEM-1.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, or prokaryotic cells. The cell line or host cell is preferably of mammalian origin, but cell lines or host cells of non-mammalian origin may be employed, including prokaryotic cells or insect cells.

"Transfected" is used herein to include any host cell or cell line, the genome of which has been altered or augmented by the presence of at least one recombinant DNA sequence, which DNA is also referred to in the art of genetic engineering as "heterologous DNA," "exogenous DNA," "genetically engineered," "non-native," or "foreign DNA," wherein said DNA was isolated and introduced into the genome of the host cell or cell line by a process of genetic engineering. The cell lines of the present invention are typically produced by transection with a DNA sequence in a plasmid expression vector, a viral expression vector, or as an isolated linear DNA sequence. Preferably, the transfected DNA is a chromosomally integrated recombinant DNA sequence, which comprises a gene encoding HEM-1, which cell line may or may not express significant levels of autologous or "native" HEM-1.

As used herein "stringent conditions" means conditions that detect a nucleic acid molecule with at least 90% nucleotide sequence homology to the probe or primer sequence. For example, stringent conditions can include hybridization conditions in 50% formamide, 2× Denhardt's, 5× SSC, 1% SDS, and 25 µg/ml RNA at 42° C. for 16 to 18 hours, followed by washing once for 5 minutes in 2× SSC at room temperature, then once for 45 minutes in 2× SSC, 1% SDS at 52° C., followed by washing once for 45 minutes at 52° C. and 0.2× SSC, 1% SDS. See Sambrook et al., *Molecular Cloning: A Laboratory Manual*, Cold Spring Harbor Laboratory Press (2nd ed., 1989) for selection of hybridization and washing conditions.

As used herein, the term "recombinant DNA" refers to DNA that has been derived or isolated from any appropriate tissue source, that may be subsequently chemically altered in vitro, and later introduced into host cells. An example of recombinant DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Therefore, "recombinant DNA" includes completely synthetic DNA sequences, semi-synthetic DNA sequences, DNA sequences isolated from biological sources, and DNA sequences derived from introduced RNA, as well as mixtures thereof. Generally, the recombinant DNA sequence is not originally resident in the genome which is the recipient of the DNA, nor it is resident in the genome but is not expressed. As used herein, the term "chimeric" DNA sequence or molecule, refers to a DNA molecule comprising sequences derived from the genomes of two or more species that do not exchange DNA under normal conditions, or to DNA sequences which are linked in a manner that does not normally occur in the native genome.

The recombinant DNA sequence, used for transformation herein, may be circular or linear, double-stranded or single-stranded. Generally, the DNA sequence is in the form of chimeric DNA, such as plasmid DNA, that can also contain coding regions flanked by regulatory sequences which promote the expression of the recombinant DNA present in the resultant cell line. For example, the recombinant DNA may itself comprise a promoter that is active in mammalian cells, or may utilize a promoter already present in the genome that is the transformation target. Promoters useful for this purpose in eukaryotic host cells include the CMV promoter, as well as the SV 40 late promoter and retroviral LTRs (long terminal repeat elements).

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

Moreover, the general methods for isolating and purifying a recombinantly expressed protein from a host cell are well known to those in the art. Examples of the isolation and purification of such proteins are given in Sambrook et al., supra.

Aside from recombinant DNA sequences that serve as transcription units for HEM-1 or portions thereof, a portion of the recombinant DNA may be untranscribed, serving a regulatory or a structural function. The recombinant DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in host cells. Useful selectable markers are well known in the art and include, for example, antibiotic and herbicide-resistance genes, such as neo, hpt, dhfr, bar, aroA, dapA, and the like.

Reporter genes are used for identifying potentially transformed cells and for evaluating the functionality of regulatory sequences. Reporter genes which encode for easily assayable marker proteins are well known in the art. In general, a reporter gene is a gene which is not present in or expressed by the recipient organism or tissue and which encodes a protein whose expression is manifested by some easily detectable property, e.g., enzymatic activity. Preferred genes for the transformation processes of the present invention include the chloramphenicol acetyl transferase gene (cat) from Tn9 of *E. coli*, the beta-galactosidase gene of *E. coli*, and the luciferase gene from firefly *Photinus pyralis*. Expression of the reporter gene is assayed at a suitable time after the DNA has been introduced into the recipient cells.

Other elements such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The recombinant DNA can be readily introduced into the target cells by transection with an expression vector comprising a cDNA encoding HEM-1 by the modified calcium phosphate precipitation procedure of C. Chen et al., *Mol. Cell. Biol.*, 7, 2745 (1987). Transection can also be accomplished by lipofection, using commercially available kits, e.g., provided by BRL.

Sources of nucleotide sequences useful in the present invention include polyA⁺ RNA from sclerosing hemangioma cell, from which the mRNA encoding HEM-1 can be derived and used for the synthesis of the corresponding cDNA by methods known in the art.

The present invention also provides purified, isolated HEM-1 protein, which can be prepared by recombinant DNA methodologies as disclosed hereinbelow. However, since the present invention provides the amino acid sequence of human HEM-1 (FIG. 1), HEM-1 or bioactive analogs thereof can also be synthesized by the solid phase peptide synthetic method. This established and widely used method, including the experimental procedures, is described in the following references: Stewart et al., *Solid Phase Peptide Synthesis*, W. H. Freeman Co., San Francisco (1969); Merrifield, *J. Am. Chem. Soc.*, 85 2149 (1963); Meienhofer in "Hormonal Proteins and Peptides," ed.; C. H. Li, Vol. 2 (Academic Press, 1973), pp. 48–267; and Bavaay and Merrifield, "The Peptides," eds. E. Gross and F. Meienhofer, Vol. 2 (Academic Press, 1980) pp. 3–285.

The invention will be better understood by making reference to the following specific examples.

EXAMPLE 1

HEM-1 cDNA isolation and Sequence Characterization

To isolate the gene(s) that encoded a sclerosing hemangioma factor-1 which cross-reacted with PTH antibodies, a cDNA expression library was prepared from RNA derived from cultured sclerosing hemangioma cells. This library was then screened with anti-PTH antisera.

Materials and Methods

All ultraviolet spectra were recorded on a Beckman DU-70 recording spectrophotometer. DNA sequencing was carried out using di-deoxysequencing methods. The DNA sequence of a cDNA clone was verified by sequencing both strands of overlapping DNA sequences. SDS-polyacrylamide gel electrophoresis was performed by the method of Laemli.

Source of the cDNA

The history of the patient from which tumor cDNA was derived is detailed in Cai et al., supra. The patient presented initially in 1974 with a seven year history of aching in her arms and legs. Investigation revealed hypophosphatemia and osteomalacia. A 2×1.5 cm mass was noted on the distal anterior thigh. Removal of the mass shortly thereafter resulted in the cure of her symptoms and biochemical abnormalities. In 1991, she presented with similar symptoms and the tumor on her thigh was noted to have recurred. Prior to tumor excision in 1993, she was hypophosphatemic with a slightly diminished serum calcium. The tubular maximum for phosphorus reabsorption was low. Immunoreactive parathyroid hormone and parathyroid hormone-related peptide concentrations were normal. Plasma 1,25-dihydroxyvitamin D was inappropriately low. Following tumor removal, the patient's biochemical and urinary parameters returned to normal. Her tumor, on histopathological examination, was a sclerosing hemangioma.

Culture Conditions of the Excised Tumor Tissue

For the tumor-cell culture, 1.5 grams of the tumor tissue removed in 1993 was dissociated enzymatically in phosphate-buffered saline containing 0.8 percent collagenase, 0.25 percent trypsin, and 0.02 mg of DNAase per milliliter. The cells were washed once in RPMI medium and resuspended in 30 ml of RPMI medium containing 10 percent fetal bovine serum. The cells were plated into three tissue-culture dishes at a concentration of $1.3 \times 10^5$ cells per milliliter and cultured at 37° C. in a humidified atmosphere of 95 percent air and 5 percent carbon dioxide. The cells grew slowly in vitro. Conditioned medium was removed on days 2 and 8, pooled, and stored at −70° C.

Construction of a cDNA Expression Library from Sclerosing Hemangioma Cells

Day 8 tumor cells grown in RPMI medium were used to synthesize a unidirectional complementary cDNA library in λ-ZAP Express according to the manufacturer's directions (Stratagene) (see Sambrook et al., supra; Ausubel et al; *Current Protocols in Molecular Biology*, John Wiley & Sons, Inc., New York (1994)). The primary library had a titer of $1.9 \times 10^6$ pfu/ml.

Screening of Library with Antibodies Directed Against Parathyroid Hormone

The cDNA library was screened with two goat polyclonal antibodies directed against residues 1-44 and 44-68 of parathyroid hormone (Klee et al., *Clin. Chem.*, 38, 628 (1992); Kumar et al., *Am. J. Physiol.*, 266, F477 (1994)). The antibodies were initially absorbed against an *E. coli* cell lysate. The pre-absorbed antioparathyroid hormone antibodies were used to screen phage plaques that were induced to form proteins with isopropylthiogalactoside. The tiler of the antibodies was 1:5000. Methods used for titering, plating and lifting plaques on nitrocellulose filters were as recommended by the manufacturer, Stratagene. The secondary antibody used to detect primary antibodies bound to positive plaques was a rabbit anti-goat IgG conjugated to alkaline phosphatase. Color generation following attachment of secondary antibodies was carried out using the picoBlue kit from Stratagene. Blue colored plaques detected after screening the primary library were carded through to secondary and tertiary screens.

Conversion of Positive Phage Plaques into "Phagemids"

The positive phage plaques were converted into plasmids using the automatic excision procedure described by Stratagene and transformed into *E. coli* XLOLAR cells (Stratagene). Bacterial colonies containing plasmids derived from the positive phage plaques were screened with PTH antibody to ensure that the immunoreactive protein was still being synthesized. One isolated cDNA clone, clone 1, was sequenced by the dideoxy sequencing method.

Immunostaining of Tumor Block with Anti-Parathyroid Hormone Antibodies

The tumor tissue was fixed in para-formaldehyde and then embedded in paraffin. Four micrometer thick serial sections were cut and placed in silanized slides. The slides were deparaffinized in xylene, rehydrated in a series of ethanol solutions, rinsed in tap water and endogenous peroxidase activity was blocked using 3% $H_2O_2$ in 50% methanol. After a tap water rinse, sections were placed in 10 mM citric acid, pH 6.0, and treated with 5% normal goat 1.5 serum in phosphate-buffered saline, pH 7.4, containing 0.05% Tween 20 for 10 minutes and incubated separately with primary antibodies for 30 minutes (goat-anti PTH 1-44 and 44-68, 1:1000 dilution; anti-Von Willebrand, 1:750 dilution, as an endothelial cell marker) at room temperature. After thorough rinsing in tap water, all sections were treated with biotinylated goat anti-rabbit immunoglobulin G (Dako, Japan, 1:400), followed by peroxidase-labeled streptavidin (Dako, 1:500) for 30 minutes at room temperature. Sections were developed by adding 0.1M sodium acetate, pH 5.2, containing aminoethyl carbazole and $H_2O_2$ for 15 minutes. Sections were counterstained with hematoxylin and placed on a coverslip with aqueous mounting media. Parathyroid tissue was used as a positive control. Negative controls for nonspecific staining were done on tissue sections using preimmune goat serum diluted 1:1000 in place of the primary antibody.

RESULTS

Clone 1 contained a cDNA of 1146 bp (SEQ ID NO:1) and encodes a putative protein of 381 amino acids (SEQ ID NO:2) (FIG. 1). There is no resemblance to PTH in the primary structure of clone 1. The first methionine in the largest open reading frame is followed by a second methionine 140 bp downstream. There is a Kozak consensus sequence around the second ATG codon for methionine (bp 134–136) suggesting that this might be the appropriate start site for the HEM-1 product. There is a protein kinase C activation domain at amino acid residues 217 to 223, similar to one found in parathyroid hormone at residues 26-32. A potential polyadenylation signal is noted at base pairs 1051–1057. A poly $A^+$ stretch is noted at 1128 to 1146 base pairs. This is not, however, preceded by a termination codon in the sequence of clone 1. Further PCR analysis of the cDNA library with oligonucleotide primers specific to either the 5' or 3' end of the insert cDNA and primers specific to the vector, gave products that were no larger than the cDNA insert in clone 1.

Immunostaining of the tumor with antibodies against PTH showed epitopes cross-reacting with the antibody in cells lining vascular spaces. These cells also immunostained with an antibody directed against von Willebrand's factor. Thus, PTH reactive epitopes are present in endothelial cells of a sclerosing hemangioma. A cDNA clone isolated from this sclerosing hemangioma encodes an epitope(s) that cross reacts with the same antibodies.

EXAMPLE 2

In vitro Expression of HEM-1

To determine if the cDNA insert in clone 1 expressed a protein that cross-reacted with anti-PTH antibodies in a eukaryotic in vitro expression system, RNA derived form the insert was translated in a rabbit reticulocyte extract. Clone 1 was also transfected into OK cells to determine whether it expressed a protein that alters phosphate transport in kidney epithelial cells.

Materials and Methods

Translation of cRNA of PTH Immunoreactive Material

Complementary RNA from clone 1 was derived using the $T_7$ promoter sequence in pBK-CMV and $T_7$ polymerase. Clone 1 was digested with XhoI and used as a template for the transcription of a capped synthetic mRNA with $T_3$ RNA polymerase (Sambrook et al., supra; Ausubel et al., supra). The reaction mixture contained 1.5 µg of digested DNA in 40 mM Tris-HCl pH 8.0, 8 mM $MgCl_2$, 2 mM spermidine, 25 mM NaCl, 1 mM each of ATP, CTP, GTP and UTP, 1 mM DTT, 25 U of RNAGuard, 50 U of $T_3$ RNA polymerase, and 0.5 mM G(5')ppp(5')G. After 1 hour at 37° C., 10 µg of tRNA was added as a carrier, 2 U of RQ1 DNase (Promega) were added, and the incubation was continued for an additional 10 minutes at 37° C. The products were recovered by phenol extraction and ethanol precipitation.

Translation of the synthetic mRNA was in 200 µl of rabbit reticulocyte lysate prepared according to Jackson and Hunt (*Methods Enzymol.*, 96, 50 (1983)) supplemented with 250 µCi of $^{35}S$ methionine. Following translation, the reaction was adjusted to 10 mM Tris HCl, pH 8.5. 20 µl of a 1:20 dilution of anti-PTH polyclonal antibodies or 1 µl of non-immune serum was then added to 100 µl aliquots of translation products, and incubation was continued for 1 hour on ice. Antibody-selected products were recovered by the addition of 200 µl of a 1:1 slurry of protein A Sepharose in pH 8.5 buffer (10 mM Tris HCl, pH 8.5, 1 mM $MgCl_2$, 0.1M NaCl). Following an additional 1 hour incubation on ice, 300 µl of a 1:1 slurry of Sepharose was added and the mixture was transferred to disposable plastic columns for washing with 25 ml of NET2 (50 mM Tris-HCl, pH 7.5, 0.15M NaCl, 5 mM EDTA, 0.5% NP-40). Antibody selected products were eluted with two 0.5 ml washes of 0.1M glycine, pH 3.0, and recovered by precipitation with 9 volumes of acetone. Radioactive, antibody-selected products were analyzed by electrophoresis on 10% SDS-polyacrylamide gels and fluorography using Enhance (NEN) according to the manufacturer's instructions.

Transection of Opossum Kidney Epithelial (OK) Cells with HEM-1 or Control Plasmids In order to test the phosphate uptake inhibitory effect of the protein derived from clone 1, the plasmid containing the clone 1 cDNA insert in pBKCMV, was used to either transiently or permanently transfect OK cells. A LipofectAMINE transection method was used (Howley-Nelson et al., *Focus*, 15, 73 (1993)). Briefly, OK cells were seeded in six-well plates with a density of $1-2 \times 10^5$ cells/well in a 2 ml of F-12/DMEM medium with 10% fetal bovine serum (OK cell growth medium). The medium was replaced with serum-free OPTI-MEM I medium (Gibco BRL) after 24 hours and the plates were incubated in a 37° C. incubator until the cells were 50–80% confluent (about 24 hours). One ml of OPTI-MEM I medium, with a mixture of 1 µg of clone 1 chimetic DNA or pBKCMV alone (control) and 10 µl of LipofectAMINE (Gibco, BRL) was used to transfect OK cells. Twelve to twenty-four hours after the transection, 1 ml of growth medium containing 20% fetal bovine serum was added to each well. After an additional 12–24 hours, the medium was replaced by OK cell growth medium. Permanently transfected cells were selected by growing transfected cells in G418 (500 µg/ml). Sodium-dependent phosphate uptake was measured in transfected OK cells (see below).

Collection and Preparation of Dialysates form End-Stage Renal Disease Patients

Dialysates were collected from six end-stage renal disease patients dialyzed with F-80, polysulfone dialyzers (Fresenius Inc., Walnut Creek, Calif.). The molecular weight cut off of F-80 dialyzers is about 40,000 daltons. Thirty to forty liters of the dialysate were collected from each patient. The collected dialysates were concentrated with cellulose acetate CA-1211 dialyzers (Baxter Healthcare Corporation, Deerfield, Ill.). The molecular weight cutoff of CA-1211 dialyzers is about 1,000 daltons. Dialysates from each patient were concentrated to ~100 ml and dialyzed against water for 14 hours using an Amicon H1P2-43 hollow fiber cartridge dialyzer (Amicon, Beverly, Mass.). The final salt-free solution was lyophilized. The weight of the lyophilized material ranged from 0.2 to 3 grams. Fifty mg of the lyophilized dialysate from each patient was resuspended in 10 mls of OK cell medium and 50 to 500 µl of this solution was used to treat the OK cells for 2 hours before measurement of the solute transport.

Size Chromatography

A Superose 12 column (HR 16/50, Pharmacia, Piscataway, N.J.) was used with a Waters 650 Advanced Protein Purification System (Millipore, Bedford, Mass.) to separate components of the concentrated dialysate. The elution buffer contained the following: 1 mM DTT, 15 mM HEPES, 4.2 mM KCl, 120 mM NaCl, pH 7.4. The flow rate of the elution buffer was 1 ml/min. The eluate material was analyzed with a UV detector set at 214 nm wavelength. Proteins with known molecular weight were used as standards to assess the molecular weight of the eluted materials. Six milliliter fractions were collected and dialyzed against water for two days at 4° C. and then lyophilized. Each lyophilized fraction was resuspended in 0.5 ml of opossum kidney cell medium and 5 ul to 50 ul of it was used to treat OK cells before measurement of solute transport.

Measurement of Sodium-Dependent Phosphate, Alanine, and Glucose Cotransport

One hundred microliters of growth medium obtained from the tumor cell cultures on day 2, 100 µl of RPMI medium with 10 percent fetal calf serum, bovine PTH residues 1-34 ($6 \times 10^{-9}$M) or PTH vehicle was added to the opossum-kidney cells to assess their effect on sodium-dependent phosphate transport. ($Nle^8$, $Nle^{18}$, $Tyr^{34}$) bovine PTH (3-34) amide ($10^{-5}$M) was used as a PTH antagonist.

For the measurement of sodium-dependent phosphate transport, 0.1 mM dibasic potassium phosphate was included in the transport medium and [$^{32}P$] dibasic potassium phosphate was added to a final specific activity of 2 µCi per milliliter. For sodium-dependent alaninc transport, 0.1 mM L-alanine and [$^3H$]L-alanine were added (final specific activity, 1 µCi per milliliter). For glucose transport, 0.1 mM methyl-α-glycopyranoside and methyl(α-D-[$u^{14}C$] gluco) pyranoside were added (final specific activity, 0.2 µCi per milliliter). The transport of phosphate, alanine, and methyl-α-glycopyranoside was assayed separately. Each transport reaction was measured in three or four duplicate wells. Each assay included three or four blank wells to correct for solute bound to the surfaces of the cells and the well and in intercellular spaces.

Treatment of Medium Obtained form Tumor-Cell Cultures

Medium (0.5 ml) obtained on day 2 of tumor-cell culture and control medium were boiled for 10 minutes in a water bath. Medium (0.5 ml) harvested from the tumor-cell cultures was dialyzed against water at 4° C. overnight with membranes that retained particles with a molecular weight of either 8 kd or larger or 25 kd or larger. The effect of the boiled or dialyzed medium on phosphate transport in opossum-kidney cells was measured.

Assays

Enzyme immunoassay was used to measure cAMP. The presence of PTH-like substances in media from tumor-cell cultures with an immunochemiluminometric midregion assay. This assay measures intact PTH and N-terminal PTH fragments but not C-terminal PTH (53-84). RPMI medium containing either 10 percent fetal calf serum or 10 percent fetal calf serum conditioned by the growth of Chinese hamster-ovary cells was used as the control medium. PTH-related protein was measured by radioimmunoassay with antibodies against PTH-related protein.

RESULTS

Figure 4:
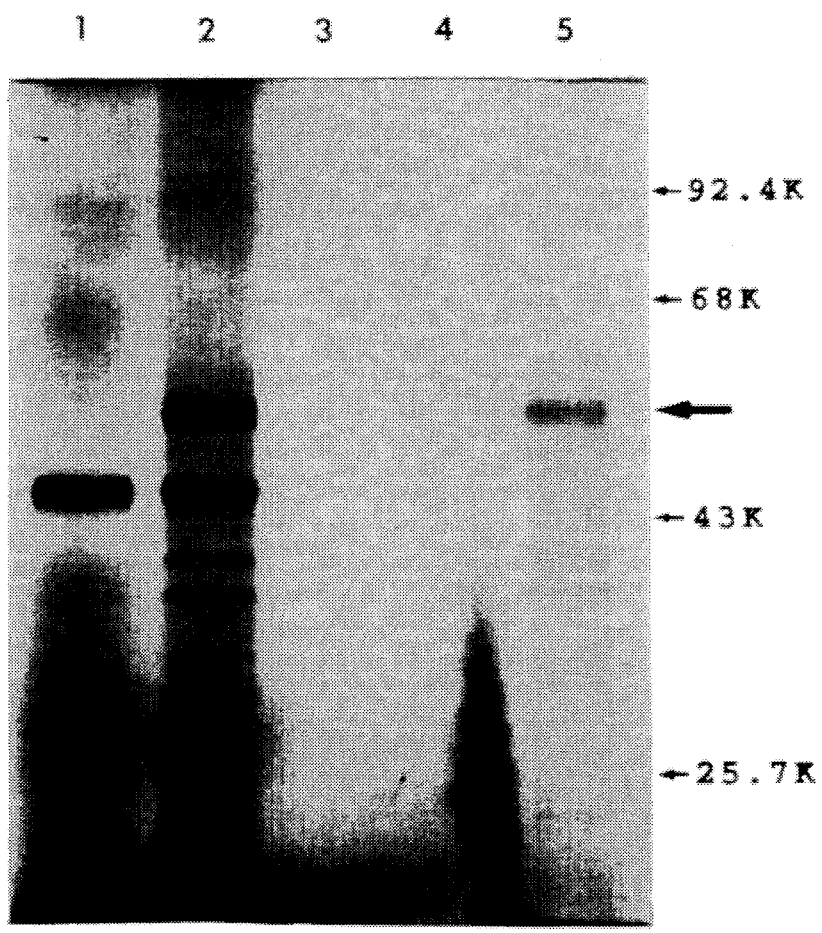
FIG. 4 depicts the $^{35}$S-labeled translation products derived from cRNA from a cDNA clone of HEM-1. Synthetic mRNA transcribed from a cDNA clone of HEM-1 was translated in a rabbit reticulocyte lysate system (lane 2). Control reactions contained no synthetic mRNA (lane 1). The $^{35}$S-labeled translation products were divided into aliquots and electrophoresed prior to (lane 2), or following immunoprecipitation with antiserum against PTH (lane 5), or with non-immune serum. The bands were visualized by autoradiography.

FIG. 4 shows an autoradiogram obtained following translation of clone 1 cRNA in a rabbit reticulocyte translation assay. The product, which was immunoprecipitated by anti-parathyroid hormone antibodies, has an Mr of 50,000 (lanes 2 and 5). Non-immune antiserum did not precipitate a band of Mr 50,000.

There was no difference between the sodium-dependent phosphate uptake measured on OK cells either permanently or transiently transfected with clone 1 and that measured in OK cells transfected with the vector plasmid alone.

Figure 5:
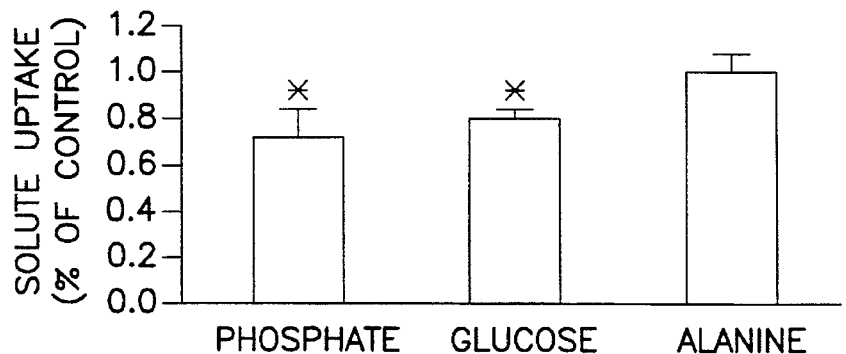
FIG. 5 shows the effect of concentrated dialysates obtained from patients with end-stage renal disease on sodium-dependent phosphate, glucose or alanine transport in Opossum-kidney epithelial cells (OK cells) (*p<0.05).
Figure 6:
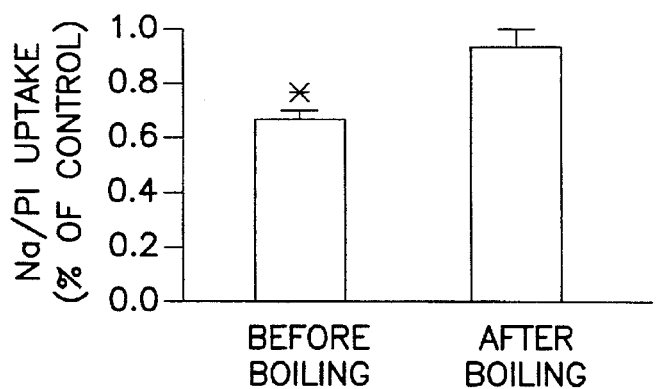
FIG. 6 shows the effect of boiling dialysates obtained from patients with end-stage renal disease on phosphate transport inhibition in OK cells. (*p<0.05).
Figure 7:
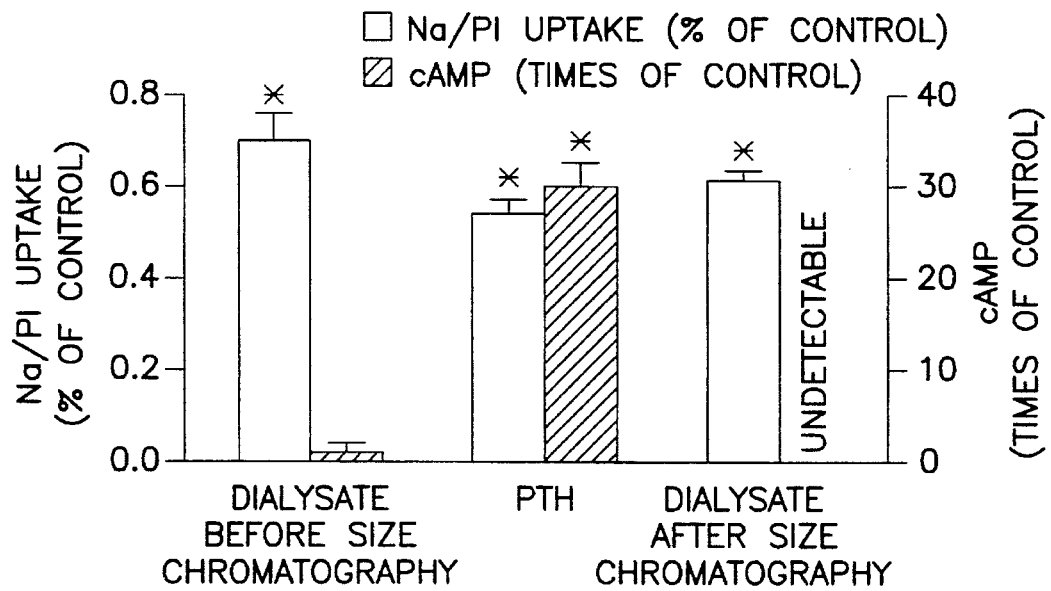
FIG. 7 shows the effect of concentrated dialysates before and after size exclusion chromatography from patients with end-stage renal disease on cAMP concentration of OK cells.

When concentrated dialysates obtained from patients with end-stage renal disease were tested for sodium-dependent phosphate uptake, a decrease in sodium-dependent phosphate uptake was observed in the presence of dialysate concentrates (FIG. 5). In addition, there was also inhibition of glucose transport but not alanine transport (FIG. 5). FIG. 6 shows that the substance or substances that inhibit sodium-dependent phosphate transport in kidney epithelia are heat labile. The inhibition of sodium-dependent phosphate transport by dialysates obtained from patients with end-stage renal disease is not dependent upon the production of cAMP (FIG. 7). When assessed by size exclusion chromatography, the phosphate inhibitory activity is present in a fraction with a molecular weight between 20,000 and 30,000 daltons.

A candidate factor derived from a sclerosing hemangioma that alters phosphate transport in cultured kidney cells, alters transport by at least two fold relative to kidney cells exposed to $6 \times 10^{-9}$M bovine PTH 1-34 when solute uptake is measured in mmol/mg of protein. This factor will not significantly inhibit alanine and glucose transport, or increase the accumulation of cAMP. Moreover, this alteration in phosphate transport will not be blocked by Nle$^8$, Nle$^{18}$, Tyr$^{34}$-bovine PTH (3-34) amide ($10^{-5}$M), a PTH antagonist.

DISCUSSION

Tumors associated with osteomalacia, such as the sclerosing hemangioma described above, secrete a substance that inhibits the renal tubular reabsorption of phosphate. A factor produced by cultured sclerosing hemangioma cells inhibits sodium-dependent phosphate transport in cultured opossum kidney cells. The effect of this substance appears to be specific for phosphate as glucose and alanine transport are not altered by this factor. Unlike parathyroid hormone, the factor produced by the tumor, causes an inhibition of sodium-dependent phosphate transport without increasing concentrations of cAMP in the supernatant media of opossum kidney cells. The substance that produces an inhibition of sodium-dependent phosphate transport is heat labile and of a molecular weight between 8,000 and 25,000 daltons. In addition, we have detected parathyroid hormone-like reactivity in the supernatants of cultured sclerosing hemangioma cells as well as in tumor sections themselves.

A cDNA clone of HEM-1 was isolated from a cDNA library derived from a sclerosing hemangioma associated with osteomalacia. HEM-1 encodes a protein that interacts with antibodies directed against the amino terminal and mid-region of parathyroid hormone. Several lines of evidence suggest that this factor is produced by the tumor cells. First, supernatant medium from cultured tumor cells contains material that binds to anti-parathyroid hormone antibodies. Second, tumor tissue immunostains with anti-PTH antibody and these stained tumor cells are of vascular origin, inasmuch as they also immunostain with an antibody directed against von Willebrand's factor. Third, a cDNA library derived from day 8 tumor cells expresses a protein capable of immunoreacting with anti-parathyroid hormone antibodies. Fourth, a synthetic mRNA derived from a cDNA clone derived from the cultured sclerosing hemangioma cells directs the synthesis of a protein that is immunoprecipitated by anti-parathyroid hormone antibodies.

Sequence analysis of the protein shows that it encodes for a 381 amino acid protein in its longest open reading frame. The ATG codon encoding a methionine residue at bp 133–135 has a Kozak consensus sequence for translation initiation. A poly A+ stretch at the 3' end of the sequence is not likely to be the 3' most poly A+ stretch as no stop codon is present in the continuous open reading frame that spans the entire cDNA insert. At amino acid residues 217-223 (nucleotides 650–670), there is a domain similar to the protein kinase C activation domain present at residues 28 to 32 of the PTH molecule (Jouishomme et al., J. Bone Min. Res., 9, 943 (1994)). Whether this is the epitope recognized by the anti-parathyroid hormone antibodies is unknown. There are several potential sites in the protein at which post-translation modification can occur by phosphorylation or myristylation. The functional significance of these sites remains undetermined.

Factors similar to those present in tumor media were also present in dialysates of patients with end-stage renal disease. Inhibition of sodium-dependent phosphate transport in renal epithelia were present in concentrated dialysates of patients dialyzed with polysulfone dialysers that have a 30,000 to 40,000 dalton molecular weight cutoff. These dialysates also contained a factor that inhibited sodium-dependent glucose uptake in cultured renal cells. Whether a single or multiple factor present in dialysates inhibited phosphate and glucose transport is unknown.

These results suggest that there are inhibitors of sodium-dependent phosphate transport of renal epithelia present in patients with tumor-induced osteomalacia and in patients with end-stage renal disease. The factor elaborated by sclerosing hemangioma cells, HEM-1, may be increased in diseases associated with hypophosphatemia such as X-linked hypophosphatemic rickets, in addition to being elaborated by patients with tumor-induced osteomalacia (Econs et al., N. Eng. J. Med., 330, 1679 (1994); Meyer et al., J. Bone Min. Res., 4, 493 (1989); Nesbitt et al., J. Clin. Invest., 89, 1453 (1992)). Conversely, the syndrome of tumoral calcinosis that is characterized by elevated serum phosphate concentrations may represent a deficiency of HEM-1 (Lufkin et al., J. Clin. Endocrinol. Metab., 56, 1319 (1983)). Patients with end-stage renal disease often accumulate phosphate and frequently develop secondary hyperparathyroidism as a result of phosphate retention. Such individuals would certainly be helped by the elaboration of a factor that would cause phosphaturia. Hence, the presence of inhibitors of sodium-dependent phosphate transport in dialysates of patients with end-stage renal disease suggests that they are elaborated in response to retained phosphate. Whether or not HEM-1 or factors like it are present in normal physiologic states, and whether or not HEM-1 concentrations are altered by the administration of phosphate or by phosphate deprivation remains to be determined.

All publications and patent applications are herein incorporated by reference to the same extent as if each individual publication or patent application was specifically and individually indicated to be incorporated by reference. It will be apparent to one of ordinary skill in the art that many changes and modifications can be made in the invention without departing from the spirit or scope of the appended claims.

What is claimed is:

1. An isolated and purified DNA molecule comprising a DNA segment encoding hemangioma factor-1.

2. An isolated and purified DNA molecule comprising a DNA sequence encoding hemangioma factor-1 of SEQ ID NO:1.

3. An expression cassette comprising: an isolated and purified DNA molecule comprising a DNA segment encoding hemangioma factor-1 operably linked to a promoter functional in a host cell.

4. The expression cassette of claim 3 wherein the DNA segment is SEQ ID NO:1.

5. An isolated protein having an amino acid sequence corresponding to SEQ ID NO:2.

6. A host cell, the genome of which has been augmented by a non-native DNA sequence encoding hemangioma factor-1.

7. The host cell of claim 6 wherein the DNA sequence encoding hemangioma factor-1 is SEQ ID NO:1.

8. The host cell of claim 6 wherein the cell is a prokaryotic cell.

9. The host cell of claim 6 wherein the cell is a eukaryotic cell.

10. The host cell of claim 6 wherein the non-native DNA sequence has been chromosomally integrated into the host cell genome.

11. The isolated and purified DNA molecule of claim 1 wherein the DNA encodes a protein recognized by anti-parathyroid antibodies.

12. A method of introducing and expressing an exogenous hemangioma factor-1 in a host cell comprising:

(a) transforming host cells in vitro with an expression cassette comprising a DNA molecule encoding the exogenous hemangioma factor-1 operably linked to a promoter functional in the host cell; and (b) identifying a transformed host cell which expresses the DNA molecule.

13. The method of claim 12 further comprising isolating protein expressed from the DNA molecule in the host cell.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 1146 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO: 1:

| | | | | | | |
|---|---|---|---|---|---|---|
| GGCACGAGCT | CGTGCCGATT | CTGTTTTGAA | TATAGCCAGA | GGAAAAAAGC | ATGGAGAAAA | 60 |
| AACTAGGAGA | GTGTCTTCTC | ATAAACAACC | AGCCTTGAAG | GCTACAAGTG | ACAAGGAAAA | 120 |
| TTCTGTTCCG | AATATGGCCA | CAGAAACAAA | GGATGAACAA | ATATCTGGGA | CAGTGTCTTC | 180 |
| TCAGAAACAA | CCAGCCTTGA | AGGCTACAAG | TGACAAGAAA | GATTCTGTTT | CGAATATACC | 240 |
| CACAGAAATA | AAGGATGGAC | AACAATCTGG | AACAGTGTCT | TCTCAGAAAC | AACCGGCCTG | 300 |
| GAAGGCTACA | AGTGTCAAGA | AAGATTCTGT | TTCGAATATA | GCCACAGAGA | TAAAGGATGG | 360 |
| ACAAATACGT | GGGACAGTGT | CTTCTCAGAG | ACAACCAGCC | TTGAAGGCTA | CAGGTGATGA | 420 |
| GAAAGATTCT | GTTTCGAATA | TAGCCAGAGA | AATAAAGGAT | GGAGAAAAAT | CTGGGACAGT | 480 |
| GTCTCCTCAG | AAACAATCGG | CCCAGAAGGT | TATATTTAAA | AAGAAAGTTT | CTCTTTTGAA | 540 |
| TATTGCCACA | AGAATAACGG | GCGGTTGGAA | ATCTGGAACA | GAGTATCCTG | AGAATCTGCC | 600 |
| CACCTTGAAG | GCTACAATTG | AAAATAAAAA | TTCTGTTCTG | AATACAGCCA | CCAAAATGAA | 660 |
| AGATGTACAA | ACATCCACAC | CAGAACAAGA | CTTAGAAATG | GCATCAGAGG | GAGAGCAAAA | 720 |
| GAGGCTTGAA | GAATATGAAA | ATAACCAGCC | ACAGGTGAAA | AACCAAATAC | ATTCTAGGGA | 780 |
| TGACCTTGAT | GACATAATTC | AGTCATCTCA | AACAGTCTCA | GAGGACGGTG | ACTCGCTTTG | 840 |
| CTGTAATTGT | AAGAATGTCA | TATTACTCAT | TGATCAACAT | GAAATGAAGT | GTAAAGATTG | 900 |
| TGTTCACCTA | TTGAAAATTA | AAAAGACATT | TTGTTTATGT | AAAAGATTAA | CAGAACTTAA | 960 |
| AGATAATCAC | TGTGAGCAAC | TTAGAGTAAA | AATTCGAAAA | CTGAAAAATA | AGGCTAGTGT | 1020 |
| ACTACAAAAG | AGACTATCTG | AAAAAGAAGA | AATAAAATCG | CAGTTAAAGC | ATGAAACACT | 1080 |
| TGAATTGGAA | AAAGAACTCT | GTAGTTTGAG | ATTTGCCATA | CAGCAAGAAA | AAAAAAAAA | 1140 |
| AAAAAA | | | | | | 1146 |

( 2 ) INFORMATION FOR SEQ ID NO: 2:

( i ) SEQUENCE CHARACTERISTICS:
        ( A ) LENGTH: 381 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 2:

```
Ala  Arg  Ala  Arg  Ala  Asp  Ser  Val  Leu  Asn  Ile  Ala  Arg  Gly  Lys  Lys
1                   5                        10                       15

His  Gly  Glu  Lys  Thr  Arg  Arg  Val  Ser  Ser  His  Lys  Gln  Pro  Ala  Leu
              20                       25                       30

Lys  Ala  Thr  Ser  Asp  Lys  Glu  Asn  Ser  Val  Pro  Asn  Met  Ala  Thr  Glu
              35                       40                       45

Thr  Lys  Asp  Glu  Gln  Ile  Ser  Gly  Thr  Val  Ser  Ser  Gln  Lys  Gln  Pro
          50                       55                       60

Ala  Leu  Lys  Ala  Thr  Ser  Asp  Lys  Lys  Asp  Ser  Val  Ser  Asn  Ile  Pro
65                       70                       75                       80

Thr  Glu  Ile  Lys  Asp  Gly  Gln  Gln  Ser  Gly  Thr  Val  Ser  Ser  Gln  Lys
                    85                       90                       95

Gln  Pro  Ala  Trp  Lys  Ala  Thr  Ser  Val  Lys  Lys  Asp  Ser  Val  Ser  Asn
              100                      105                      110

Ile  Ala  Thr  Glu  Ile  Lys  Asp  Gly  Gln  Ile  Arg  Gly  Thr  Val  Ser  Ser
              115                      120                      125

Gln  Arg  Gln  Pro  Ala  Leu  Lys  Ala  Thr  Gly  Asp  Glu  Lys  Asp  Ser  Val
          130                      135                      140

Ser  Asn  Ile  Ala  Arg  Glu  Ile  Lys  Asp  Gly  Glu  Lys  Ser  Gly  Thr  Val
145                      150                      155                      160

Ser  Pro  Gln  Lys  Gln  Ser  Ala  Gln  Lys  Val  Ile  Phe  Lys  Lys  Lys  Val
                    165                      170                      175

Ser  Leu  Leu  Asn  Ile  Ala  Thr  Arg  Ile  Thr  Gly  Gly  Trp  Lys  Ser  Gly
               180                      185                      190

Thr  Glu  Tyr  Pro  Glu  Asn  Leu  Pro  Thr  Leu  Lys  Ala  Thr  Ile  Glu  Asn
          195                      200                      205

Lys  Asn  Ser  Val  Leu  Asn  Thr  Ala  Thr  Lys  Met  Lys  Asp  Val  Gln  Thr
     210                      215                      220

Ser  Thr  Pro  Glu  Gln  Asp  Leu  Glu  Met  Ala  Ser  Glu  Gly  Glu  Gln  Lys
225                      230                      235                      240

Arg  Leu  Glu  Glu  Tyr  Glu  Asn  Asn  Gln  Pro  Gln  Val  Lys  Asn  Gln  Ile
                    245                      250                      255

His  Ser  Arg  Asp  Asp  Leu  Asp  Asp  Ile  Ile  Gln  Ser  Ser  Gln  Thr  Val
               260                      265                      270

Ser  Glu  Asp  Gly  Asp  Ser  Leu  Cys  Cys  Asn  Cys  Lys  Asn  Val  Ile  Leu
          275                      280                      285

Leu  Ile  Asp  Gln  His  Glu  Met  Lys  Cys  Lys  Asp  Cys  Val  His  Leu  Leu
     290                      295                      300

Lys  Ile  Lys  Lys  Thr  Phe  Cys  Leu  Cys  Lys  Arg  Leu  Thr  Glu  Leu  Lys
305                      310                      315                      320

Asp  Asn  His  Cys  Glu  Gln  Leu  Arg  Val  Lys  Ile  Arg  Lys  Leu  Lys  Asn
                    325                      330                      335

Lys  Ala  Ser  Val  Leu  Gln  Lys  Arg  Leu  Ser  Glu  Lys  Glu  Glu  Ile  Lys
               340                      345                      350

Ser  Gln  Leu  Lys  His  Glu  Thr  Leu  Glu  Leu  Glu  Lys  Glu  Leu  Cys  Ser
          355                      360                      365

Leu  Arg  Phe  Ala  Ile  Gln  Gln  Glu  Lys  Lys  Lys  Lys
          370                      375                 380
```